United States Patent [19]
Pepper et al.

[11] Patent Number: 5,989,255
[45] Date of Patent: Nov. 23, 1999

[54] ORTHOPAEDIC DONE SCREW APPARATUS

[75] Inventors: John R. Pepper, Germantown;
Anthony H. James, Bartlett, both of Tenn.; Roy Sanders, Tampa, Fla.;
Donna D. Holland, Atlanta, Ga.

[73] Assignee: Smith & Nephew, Memphis, Tenn.

[21] Appl. No.: 09/130,271

[22] Filed: Aug. 6, 1998

[51] Int. Cl.⁶ .................................................. A61B 17/56
[52] U.S. Cl. .............................................. 606/73; 606/61
[58] Field of Search ................................ 606/60, 61, 72, 606/73

[56] References Cited

U.S. PATENT DOCUMENTS

| | | | |
|---|---|---|---|
| 5,100,405 | 3/1992 | McLaren | 606/72 |
| 5,250,049 | 10/1993 | Michael | 606/72 |
| 5,395,371 | 3/1995 | Miller et al. | 606/61 |
| 5,591,207 | 1/1997 | Coleman | 606/232 |

*Primary Examiner*—Michael Buiz
*Assistant Examiner*—Daphna Shai
*Attorney, Agent, or Firm*—Garvey, Smith, Nehrbass, & Doody, L.L.C.

[57] ABSTRACT

A bone screw apparatus and method of implantation provides a bone screw having an elongated shaft of an oversized length with proximal and distal end portions. The distal end portion of the shaft has a cutting head. The proximal end portion of the shaft is sized and shaped to accept a driver tool, such as a drill chuck. The shaft is externally threaded along a majority of its length. A pair of opposed longitudinally extending circumferentially spaced flat surfaces are provided along the shaft. A removable head with a central opening enables the head to slide along the shaft proximally to distally. A ratcheting mechanism prevents movement of the head along the shaft in but one direction. A central opening of the head is shaped to conform to the shaped surfaces of the shaft, so that the head and shaft can be rotated as a unit by engaging and rotating the head. The tool receptive surface portion of the head includes intersecting external surfaces of the head spaced radially away from the shaft during use.

25 Claims, 6 Drawing Sheets

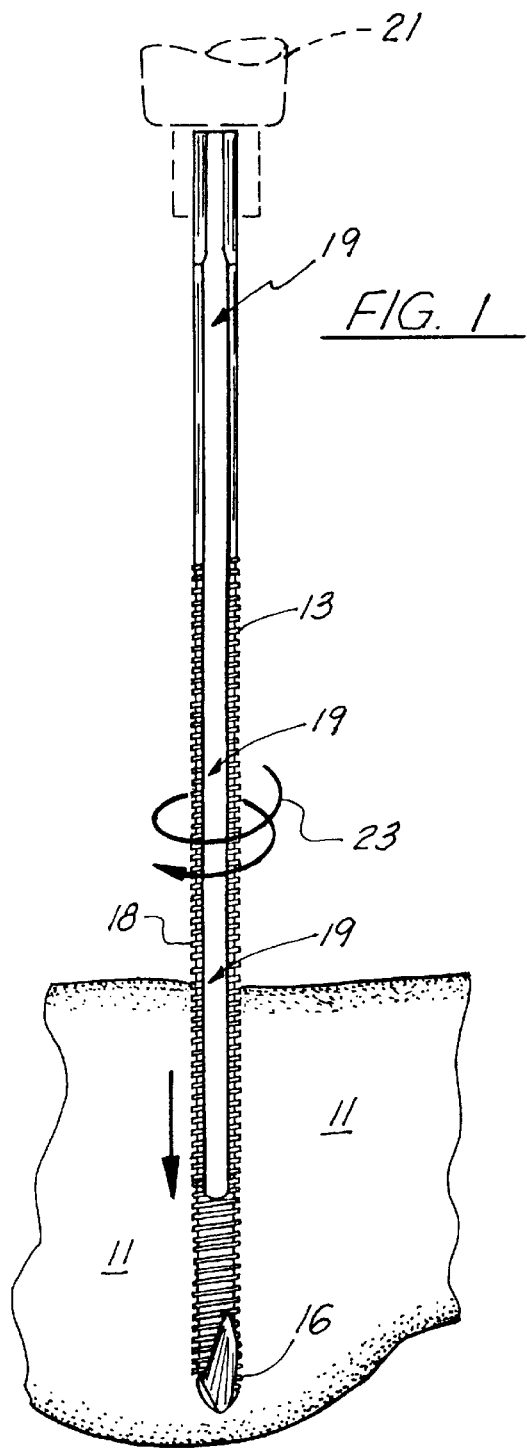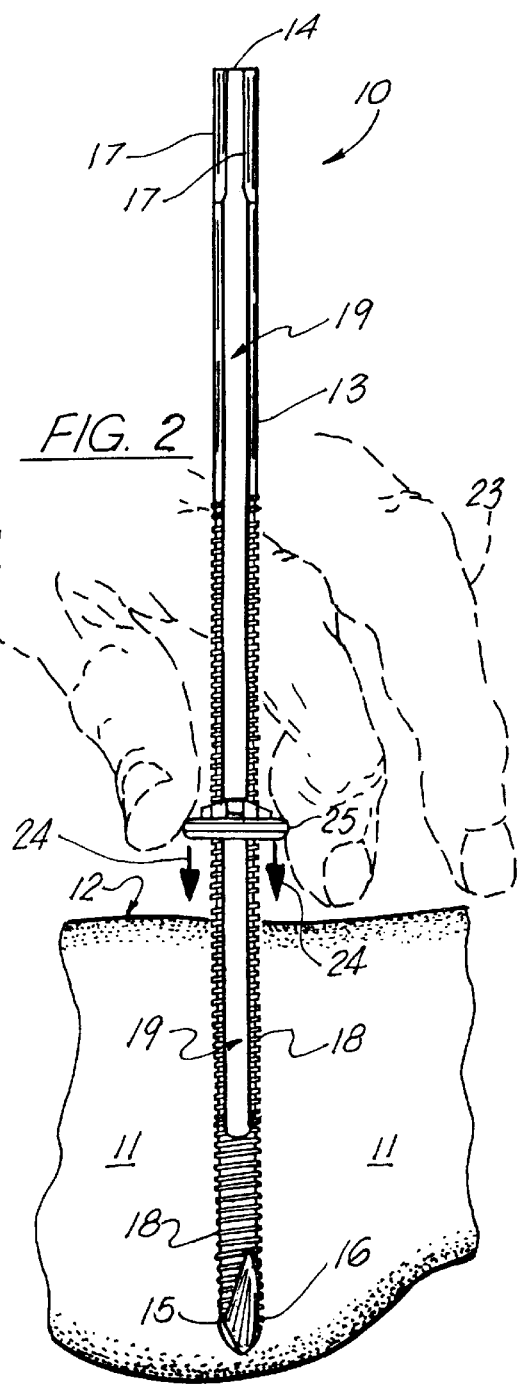

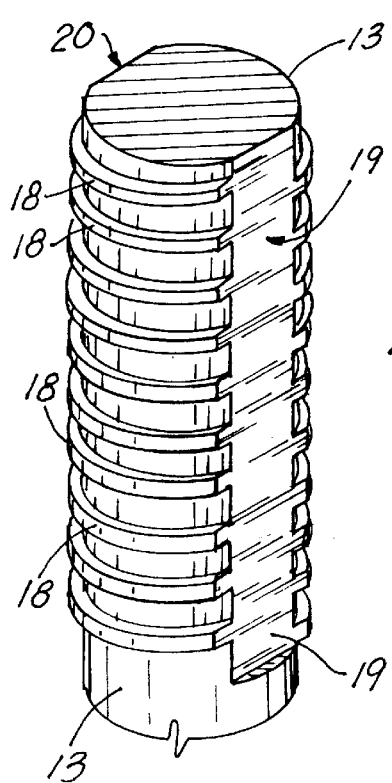
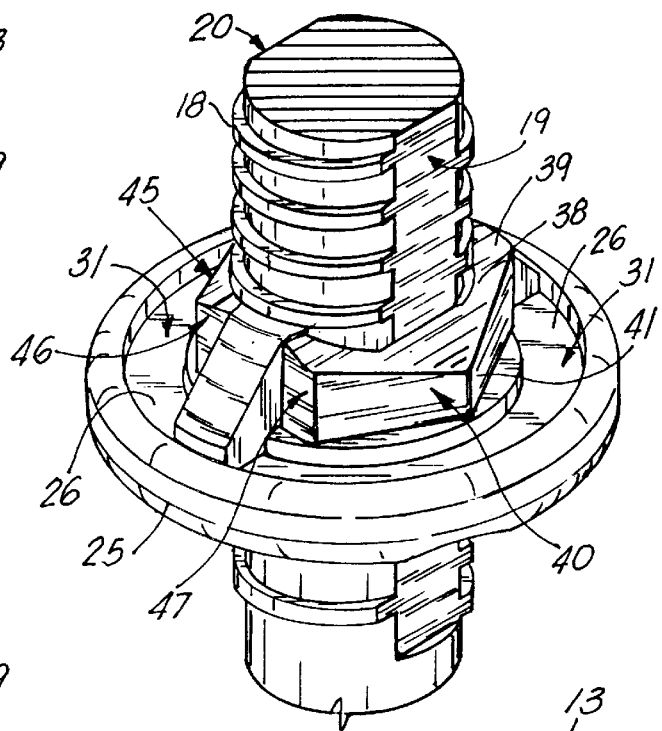
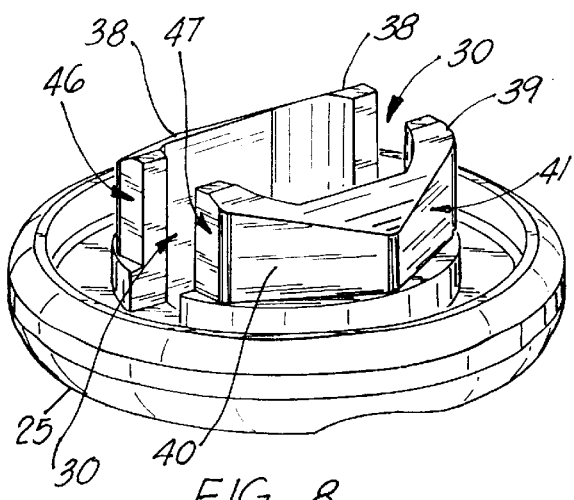
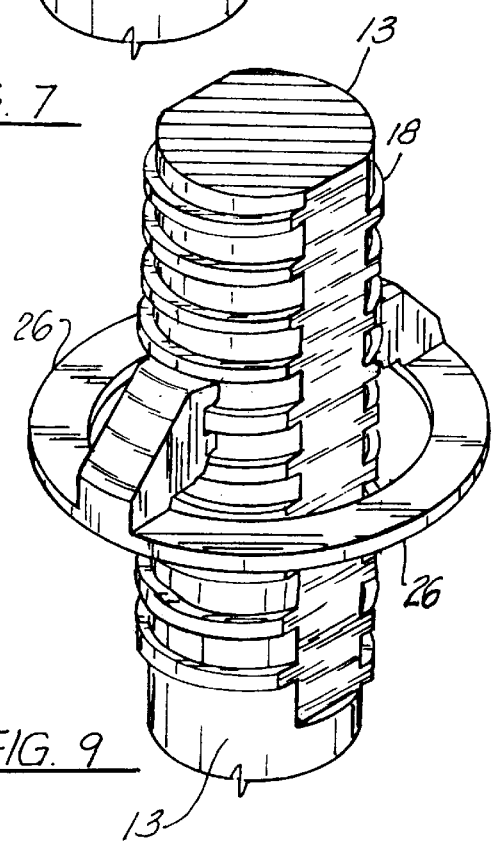
FIG. 6
FIG. 7
FIG. 8
FIG. 9

ORTHOPAEDIC DONE SCREW APPARATUS

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic bone screws and more particularly to an improved orthopaedic bone screw apparatus that can be custom fitted to a patient's bone tissue by two moving parts of the bone screw apparatus that include an elongated shank and a shaped head portion that slides over the shank. More particularly, the present invention relates to an improved orthopaedic bone screw apparatus having an elongated shank and sliding head portion with a ratcheting washer that fits over the shank and enables movement in one direction toward the patient's bone tissue but disallows sliding movement in the opposite direction.

2. General Background of the Invention

During orthopaedic surgery, bone screws are often employed. Some bone screws are embedded deep into a patient's bone tissue for affixing implants to the patient's bone tissues such as intramedullary nails. The surgeon does not always know exactly the thickness of a patient's bone tissue will be such as for example of thickness of a patient's femur. Therefore, it would be desirable for the surgeon to be able to custom size a bone screw to fit a particular patient during a particular operation.

A published PCT application PCT WO98/01079 discloses a cortical bone screw assembly comprising a shaft with a threaded section and a cutting and self-tapping end section. The assembly includes a nut which includes a resilient body. The resilient body can expand to allow translational movement of he nut along the shaft, but when such radial expansion is prevented so is such translational movement. However, the nut can still be moved along the shaft by rotation on the trhead. This enables the nut to be advanced rapidly along an exposed length of shaft, but when it enters a restricted volume which prevents expansion of the resilient body, further advance can only be achieved by relative rotation.

BRIEF SUMMARY OF THE INVENTION

The present mention provides an improved bone screw apparatus for use in orthopaedic surgery. The apparatus includes an elongated shaft having proximal and distal end portions, the distal end portion having a cutting head, and the proximal end portion being sized and shaped to fit a driver tool such as a drill chuck.

The shaft is preferably externally threaded along at least a portion of its length. A plurality of longitudinally extending, circumferentially spaced apart surfaces extend along the shaft.

A removable head portion with a central opening enables the head to slide along the shaft.

A washer nests in an annular groove of the removable head portion. The washer has a pair of opposed ratcheting members that only allow the washer to travel in a single direction when it is combined with the removable head portion.

This construction provides a means for preventing movement of the head along the shaft in a direction that would remove the head from the shaft proximally.

The removable head has an enlarged central annular portion that provides a number of flat surfaces thereon (for example eight) that define a place for attachment of a driver tool such as a hexagonally-shaped driver tool.

The tool receptive surface portion of the head includes intersecting external surfaces of the head that are spaced radially away from the shaft during use. These surfaces accept a driver tool for rotating the head and the connected shaft.

The shaft can be threaded along a majority of its length.

There are preferably two (2) longitudinally extending surfaces that are positioned about one hundred eighty (180°) degrees apart on the shaft.

A means for preventing movement of the head in one direction is defined by a pair of opposed arms with ratcheting portions thereon.

The head preferably has a convex annular distal surface that carries cutting blades thereon.

The washer provides internally threaded portions for engaging the external threads of the shaft.

The head and washer define a pair of independently movable, separable members.

A method of implanting with a bone screw to a patient's bone tissue is provided by the present invention.

The method includes the inserting of a bone screw shaft into a patient's bone tissue, the shaft having an external surface with shaped longitudinally extending portions thereon.

The method includes placing a removable head on the shaft after the shaft is embedded in step "a" by sliding the head proximally to distally along the shaft, until the head engages the patient's bone tissue.

The shaft can be severed proximally of the head once the shaft and head are in embedded in the selected bone tissue.

The head and shaft interlock and rotate together. Eventually, this enables surgeon to remove the assembly of shaft and head by rotating the head with a driver tool.

In the method of the present invention, a head is provided that is a two-part structure that includes first in second interlocking head segments and further comprising the step of connecting the first second head segments together.

The method can further comprise the step of engaging the threads of the shaft within internally threaded portion of the head. The shaft is preferably threaded along a majority of its length.

The method further comprises the steps of sliding the head to position next to the patient's bone tissue and the rotating the head relative to the shaft until the head engages and cuts the patient's bone tissue with cutting elements that countersink the head.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a perspective elevational view of the preferred embodiment of the apparatus of present invention;

FIG. 2 is a perspective elevational view of the preferred embodiment of the apparatus of present invention showing the head and washer portions attached to the shaft portion;

FIG. 6 is a fragmentary perspective view of the preferred embodiment of the apparatus of present invention illustrating the shaft portion thereof;

FIG. 7 is a fragmentary perspective view of the preferred embodiment of the apparatus present invention showing the shaft, head and washer portions thereof;

FIG. 8 is a fragmentary perspective view of the preferred embodiment of the apparatus of present invention showing be head potion thereof;

FIG. 9 is a fragmentary perspective view of the preferred embodiment of the apparatus of the present invention showing the washer and shaft portions thereof;

DETAILED DESCRIPTION OF THE INVENTION

Figure 4:
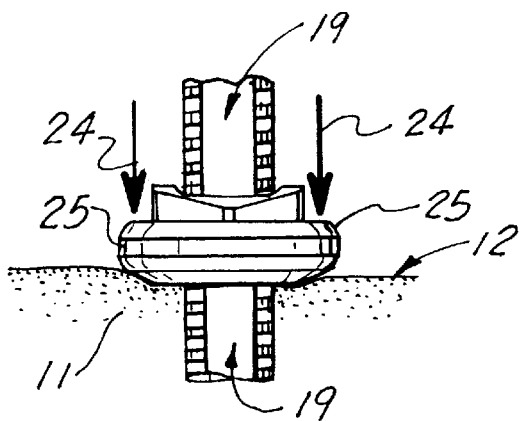
FIG. 4 is a fragmentary elevational view of the preferred embodiment of the apparatus present invention showing placement of the head and washer portions upon the shaft.

FIGS. 1–5 show generally be preferred embodiment of the apparatus of the present invention designated generally by the numeral 10 in FIG. 1. Bone screw apparatus 10 includes an elongated shank 13 that can be surgically implanted into a patient's bone tissue 11. In FIGS. 1 and 2, bone tissue 11 is shown having an outer surface 12 that is engaged by the lower or distal 15 end portion of shank 13. Shaft 13 has a proximal 14 end portion with a plurality of flat surfaces 17 that define a tool receptive surface for attachment to a drill chuck 21 or like driver tool.

Figure 5:
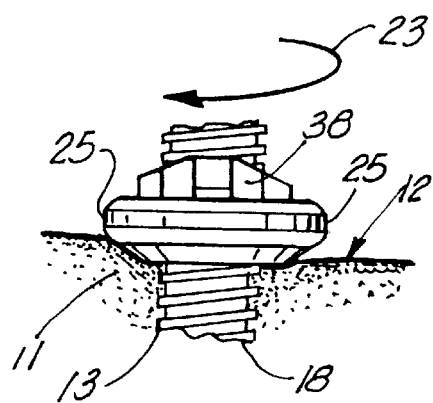
FIG. 5 is a fragmentary elevational view of the preferred embodiment of the apparatus of the present invention showing a rotational movement of washer, head and shaft.
Figure 3:
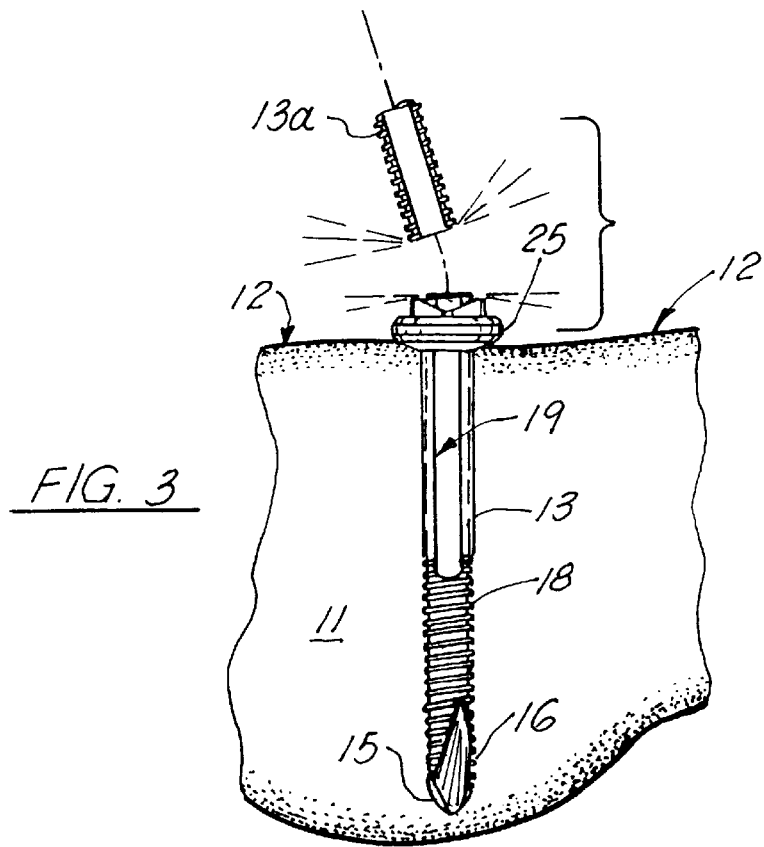
FIG. 3 is a sectional elevational view of the preferred embodiment of the apparatus of present invention illustrating separation of the upper portion of the shaft after the head, washer and shaft have been surgically placed.
Figure 10:
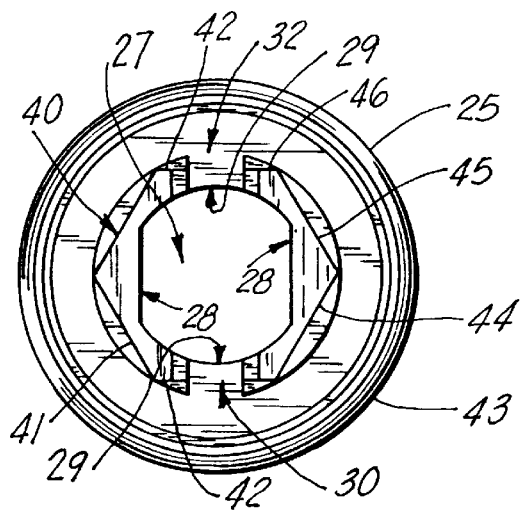
FIG. 10 is a top view of the head portion of the preferred embodiment of the apparatus of present invention.
Figure 11:
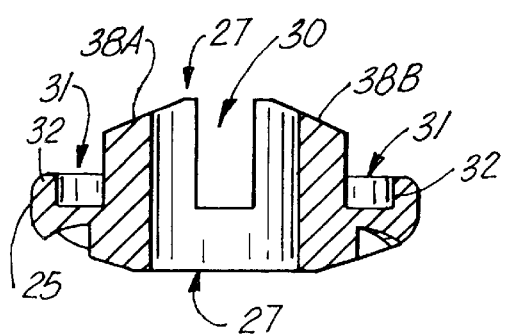
FIG. 11 is a sectional elevational view of the head portion of the preferred embodiment of the apparatus of present invention.
Figure 13:
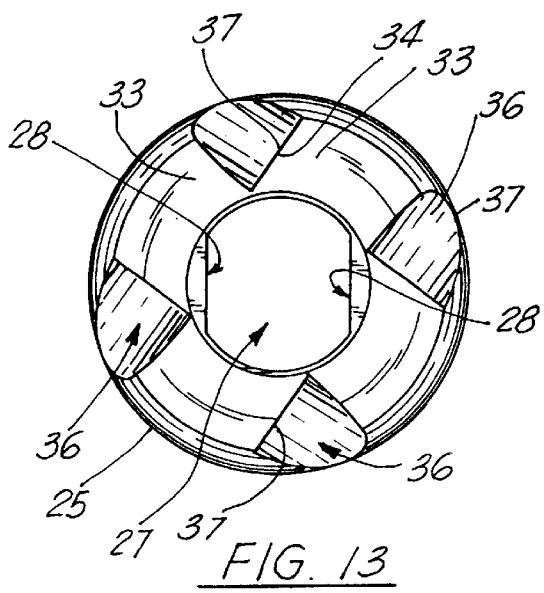
FIG. 13 is a bottom view of the head portion of the preferred embodiment of the apparatus of present invention.
Figure 12:
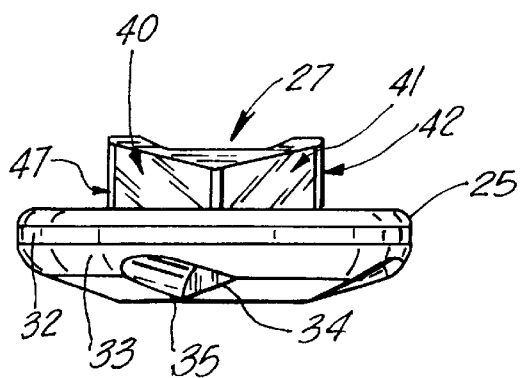
FIG. 12 is an elevational view of the preferred embodiment of the apparatus of the present invention illustrating the head portion thereof.
Figure 14:
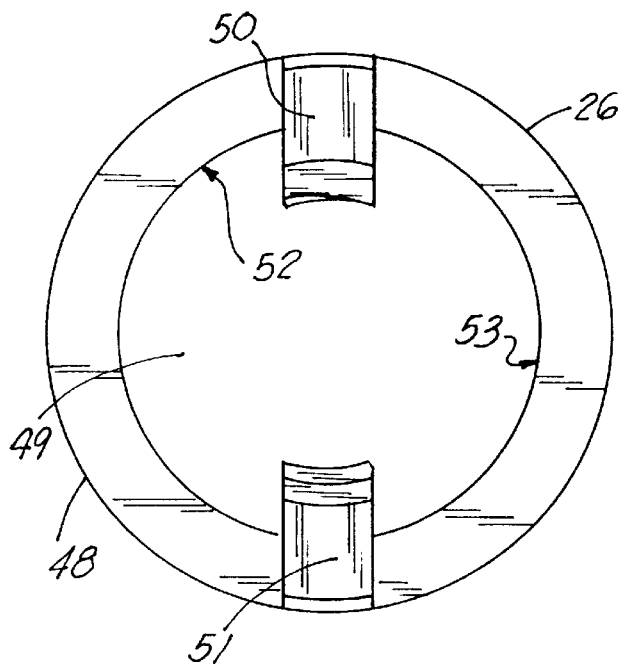
FIG. 14 is a top view of the washer portion of the preferred embodiment of the apparatus of the present invention.

Elongated shank 13 (see FIGS. 1–2 and 6–9) has a continuous helical thread 18 that extends substantially the full-length of shank 13. Shank 13 also provides a pair of longitudinally extending opposed flat surfaces 19,20. As shown in FIGS. 6–7, the surfaces 19,20 are about one hundred eighty (180°) degrees apart. The elongated shank 13 is preliminarily embedded into a patient's bone tissue 11 using drill chuck 21 (see FIG. 1). In FIGS. 1 and 5, shank 13 rotates in the direction of curved arrow 23. Once the shank 13 has been embedded into the bone tissue 11 a selected depth, the surgeon and uses his or her hand 23 to slide head 25 and washer 26 into position as shown at surface 12 of bone tissue 11. This sliding movement of the combination of head 25 and washer 26 is designated generally by the arrow 24 in FIGS. 2–3. The surgeon then cuts shank 13 as shown in FIG. 3 next to washer 25 to complete the implantation, this removing the excess, exposed shank material that is designated as 13A in FIG. 3.

In FIGS. 6–18, the construction and of head 25 and washer 26 are shown more particularly. Head 25 has a central opening 27 that fits over and conforms to the outer surface of shank 13. The opening 27 is defined by a pair of opposed flat surfaces 28 and a pair of opposed curved surfaces 29. A central raised portion 38 of head 25 has a pair of opposed slots 30 that communicate with opening 27. The central raised portion 38 includes two (2) raised sections 38A and 38B. Head 25 has an annular groove 31 surrounded by an annular shoulder 32. The underside 33 of head 25 has a plurality of cutting elements 34.

Each cutting element 34 is defined by a recess 35 that includes curved surface 36 and flat surface 40. The raised portion 38 and the raised sections 38A and 38B provide a plurality of flat surfaces 40–47 that enable a user to attach a hex driver, socket tool, or the like to the raised portion 38. The flat surfaces 40–47 can define a hexagonally-shaped surface to which a driver tool can attach. This attachment of a driver tool to raised portion 38 38 enables the entire screw apparatus 10 to be removed by rotating apparatus 10 with the driver tool in a counterclockwise direction, opposite the direction of curved arrow 23.

Figure 15:
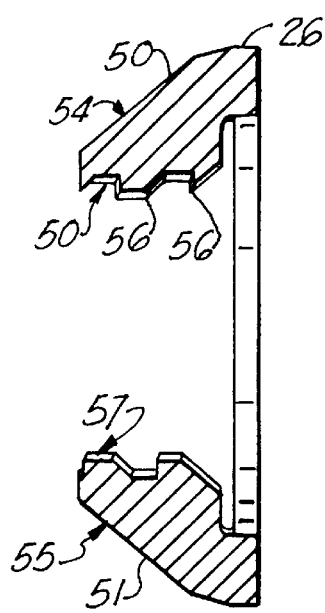
FIG. 15 is a sectional view of the washer portion of the preferred embodiment of the apparatus of the present invention.
Figure 16:
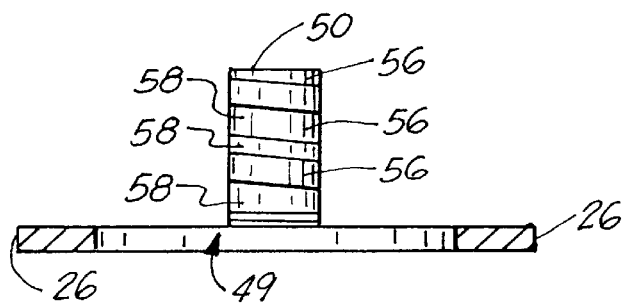
FIG. 16 is a fragmentary sectional view of the washer portion of the preferred embodiment of the apparatus of the present invention.
Figure 17:
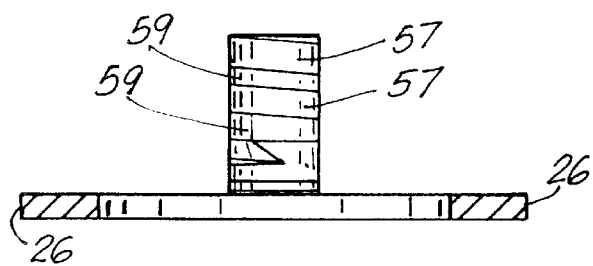
FIG. 17 is a fragmentary sectional view of the washer portion of the preferred embodiment of the apparatus and present invention.

Ratcheting washer 26 has an annular periphery 48 and a central circular opening 49. A pair of ratcheting members 50,51 are provided on washer 27, spaced apart by one hundred eighty (180°) degrees. Circular opening 49 is defined by a pair of opposed curved surfaces 52,53 shown in FIG. 14. In FIGS. 15–17, ratcheting members 50,51 are shown, each including an inclined surface 54,55 respectively. Opposite each inclined surface 54,55 there is provided thread portions 56,57 alternating with grooves 58,59 (see FIG. 15). The threads 54, 55 and grooves 58, 59 engage helical thread 18 on shank 13.

Figure 18:
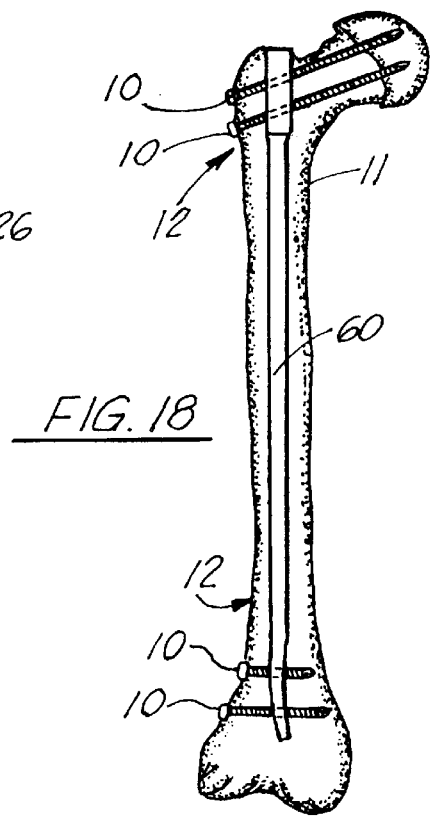
FIG. 18 is a perspective view of the preferred embodiment of the apparatus of the present invention showing implantation of an intramedullary rod and a plurality of the bone screws of the present invention securing the intramedullary rod to the patient's bone tissue.

In FIG. 18, a patient's femur is the bone tissue 11 into which a plurality of bone screws 10 have been implanted. The bone screws 10 are shown in FIG. 18 securing intramedullary rod 60 within the intramedullary canal of a patient's femur 11.

Figure 19:
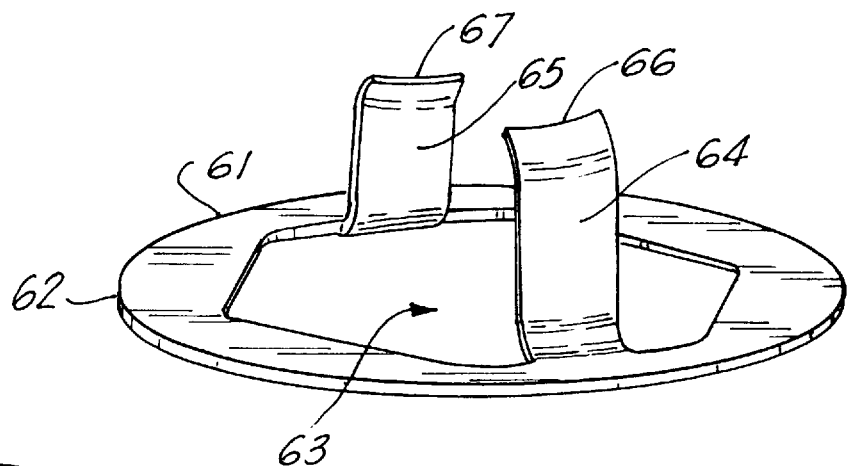
FIG. 19 is a fragmentary perspective view of an alternate embodiment apparatus of the present invention showing the washer portion thereof.
Figure 20:
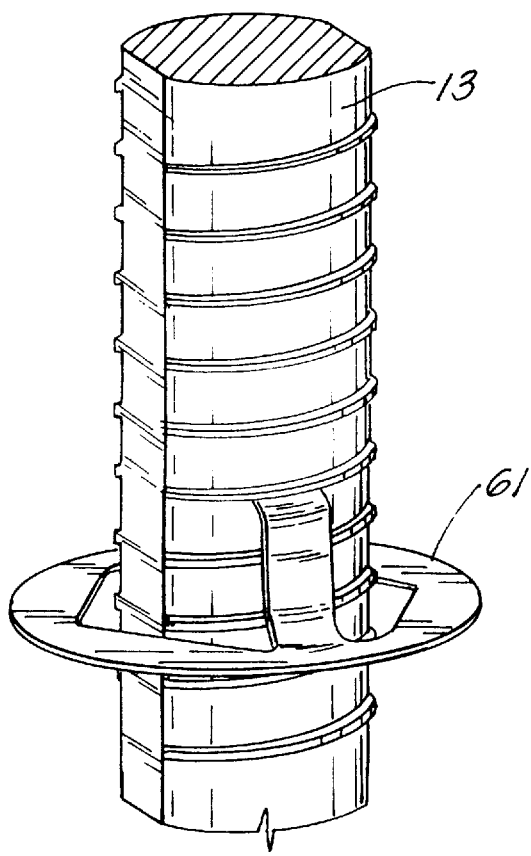
FIG. 20 is a fragmentary perspective view of the alternative embodiment of the apparatus present invention showing the washer and shaft portions thereof.
Figure 21:
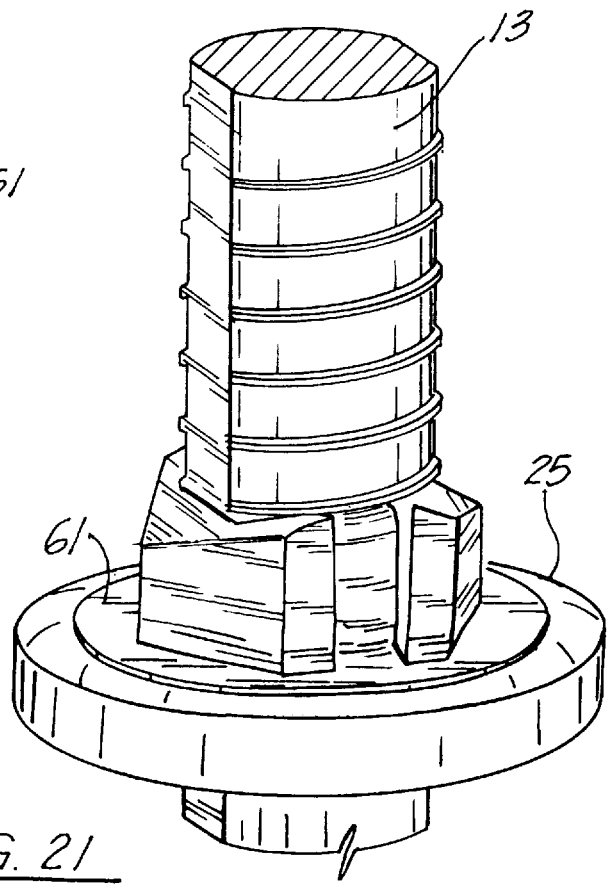
FIG. 21 is a perspective view of the alternate embodiment of the apparatus present invention.

In FIGS. 19–21, and alternate construction of the washer portion of the present invention is shown, designated generally by the numeral 61. Washer 61 and FIGS. 19–20 as a circular periphery 62 and a hexagonally-shaped opening 63. Ratcheting members 64,65 are integrally formed with ring 61. Inwardly projecting tabs 66,67 engaged the threads 18 of shank 13 during use as shown FIGS. 20 and 21. As with washer 26, the washer 61 occupies annular groove 31 of head 25 at shown in FIG. 21.

The present invention enables a surgeon to embed shank 13 a desired distance into patients' bone tissue 11. The surgeon can been attached head 25 and ratcheting washer 26 to shank 13. During use, the surgeon first places the washer 26 into annular groove 31 of head 25. The surgeon then aligns the ratcheting members 50,51 with longitudinally extending surfaces 19,20. When the ratcheting members 50,51 are aligned with the longitudinally extending surfaces 19,20 the surgeon can easily slide the combination of the head 25 and washer 26 substantially the full-length of shank 13 at showing FIG. 2.

In FIGS. 3–5, the surgeon severs excess portion 13A of shank 13 above the head 25 as shown in FIG. 3. In FIG. 5, the head 25 is sufficiently exposed so that the surgeon can attach a driver tool to rotate the head 25 and attached shank 13 in the direction of arrow 23. This causes the underside 33 of head 25 to engage the surface 12 of bone tissue 11. As the head 25 is rotating, the plurality of cutting-edges 34 countersink head 25 into bone tissue 11 at surface 12.

The following table lists the parts numbers and parts descriptions as used herein and in the drawings attached hereto.

PARTS LIST

| Part Number | Description |
| --- | --- |
| 10 | bone screw apparatus |
| 11 | bone tissue |
| 12 | bone surface |
| 13 | elongated shank |
| 13A | excess shank material |
| 14 | proximal end |
| 15 | distal end |
| 16 | cutting tip |
| 17 | flat surfaces |
| 18 | continuous helical thread |
| 19 | longitudinal flat slide surface |
| 20 | longitudinal flat slide surface |
| 21 | drill chuck |
| 22 | surgeon's hand |
| 23 | curved arrow |
| 24 | arrow |
| 25 | head |
| 26 | ratcheting washer |
| 27 | opening |
| 28 | flat surface |
| 29 | curved surface |
| 30 | slot |
| 31 | annular groove |
| 32 | annular shoulder |
| 33 | underside |
| 34 | cutting element |
| 35 | recess |
| 36 | curved surface |
| 37 | flat surface |
| 38 | central raised portion |
| 38A | raised section |
| 38B | raised section |
| 39 | central raised portion |
| 40 | flat surface |
| 41 | flat surface |
| 42 | flat surface |
| 43 | flat surface |
| 44 | flat surface |
| 45 | flat surface |
| 46 | flat surface |
| 47 | flat surface |
| 48 | annular periphery |
| 49 | circular opening |
| 50 | ratchet member |
| 51 | ratchet member |
| 52 | curved surface |
| 53 | curved surface |
| 54 | inclined surface |
| 55 | inclined surface |
| 56 | thread |
| 57 | thread |
| 58 | groove |
| 59 | groove |
| 60 | intramedullary rod |

The foregoing embodiments are presented by way of example only; the scope of the present invention is to be limited only by the following claims.

We claim:

1. A bone screw apparatus comprising;
   a) an elongated shaft having proximal and distal end portions, the distal end portion having a cutting head and the proximal end portion being sized and shaped to fit a driver tool such as a drill chuck;
   b) the shaft being externally threaded along at least a portion of its length and having at least one longitudinally extending shaped surface thereon;
   c) a removable head with a central opening that enables the head to slide along the shaft;
   d) means for preventing sliding movement of the head along the shaft distal to proximal;
   e) the head central opening being shaped to conform to the shaped surface of the shaft so that the head and shaft can be rotated as a unit by engaging and rotating the head; and
   f) a tool receptive surface portion of the head that accepts a driver tool for rotating the head and the connected shaft.

2. The bone screw apparatus of claim 1 wherein the shaft is threaded along a majority of its length.

3. The bone screw apparatus of claim 1, wherein there are two longitudinally extending surfaces positioned 180 degrees apart on the shaft.

4. The bone screw apparatus of claim 1, wherein the tool receptive surface portion of the head provides a hexagonally-shaped surface.

5. The bone screw apparatus of claim 1, wherein the means for preventing movement of the head in one direction is defined by a pair of opposed tabs with ratcheting portions.

6. The bone screw apparatus of claim 5, wherein the tabs are positioned about 180 degrees apart on opposing sides of the head.

7. The bone screw apparatus of claim 1, wherein the head has a convex annular distal surface.

8. The bone screw apparatus of claim 1, wherein the head has an internal thread for engaging the external thread of the shaft.

9. The bone screw apparatus of claim 1, wherein the head is comprised of a pair of independently movable, separable members.

10. A bone screw apparatus comprising;
    a) an elongated shaft having proximal and distal end portions, the distal end portion having a cutting head and the proximal end portion being sized and shaped to fit a driver tool such as a drill chuck;

b) the shaft being externally threaded along a majority of its length and having a plurality of longitudinally extending, circumferentially spaced apart shaped surfaces thereon;

c) a removable head with a central opening that enables the head to slide along the shaft;

d) the head having ratchets thereon that prevent sliding movement of the head along the shaft in a distal to a proximal direction;

e) the head central opening being shaped to conform to the shaped surfaces of the shaft so that the head and shaft can be rotated as a unit by engaging and rotating the head; and f) a tool receptive surface portion of the head that accepts a driver tool for rotating the head and the connected shaft.

11. The apparatus of claim 10 wherein the tool receptive surface portion of the head includes intersecting external surfaces.

12. A method of implanting a bone screw through a patient's bone tissue, comprising the steps of:

a) inserting a bone screw shaft into a patient's bone tissue, the shaft having an external surface with shaped longitudinally extending portions;

b) placing a removable head on the shaft after the shaft is embedded in step "a" by sliding the head proximally to distally along the shaft until the head engages the patient;

c) severing the shaft proximally of the head; and d) interlocking the head and shaft so that they rotate together.

13. The method of claim 12 wherein the interlocking automatically occurs in step "b".

14. The method of claim 12 wherein in steps "b" and "d" the head is a two part structure that includes first and second interlocking head segments and further comprising the step of connecting the first and second head segments together.

15. The method of claim 12, further comprising the step of engaging the threads of the shaft with an internally threaded portion of the head.

16. The method of claim 12 wherein in step "a" the shaft is threaded along a majority of its length.

17. The method of claim 12 further comprising the steps of "c" and "d", of sliding the head to a position next to the patient's bone tissue and further comprising the step of rotating the head relating to the shaft until the head engages the patient's bone tissue.

18. The method of claim 12 further comprising the step of removing the assembly of shaft and head by rotating the head with a driver tool.

19. A method of implanting a bone screw through a patient's bone tissue, comprising the steps of:

a) inserting a bone screw shaft into a patient's bone tissue, the shaft having an external surface with shaped longitudinally extending portions;

b) placing a removable head on the shaft after the shaft is embedded in step "a" by sliding the head in a proximal to distal direction along the shaft until the head engages the patient;

c) severing the shaft proximally of the head;

d) interlocking the head and shaft so that they rotate together; and e) further comprising the step between step "b" and "c" of disallowing movement of the head in a distal to proximal direction with a ratchet mechanism.

20. The method of claim 19 wherein the interlocking automatically occurs in step "b".

21. The method of claim 19 wherein in steps "b" and "d" the head is a two part structure that includes first and second interlocking head segments and further comprising the step of connecting the first and second head segments together.

22. The method of claim 19, further comprising the step of engaging the threads of the shaft with an internally threaded portion of the head.

23. The method of claim 19 wherein in step "a" the shaft is threaded along a majority of its length.

24. The method of claim 19 further comprising the steps of "c" and "d", of sliding the head to a position next to the patient's bone tissue and further comprising the step of rotating the head relating to the shaft until the head engages the patient's bone tissue.

25. The method of claim 19 further comprising the step of removing the assembly of shaft and head by rotating the head with a driver tool.

\* \* \* \* \*